United States Patent [19]

Kenna

[11] Patent Number: 5,320,115
[45] Date of Patent: Jun. 14, 1994

[54] METHOD AND APPARATUS FOR ARTHROSCOPIC KNEE SURGERY

[75] Inventor: Robert V. Kenna, Hobesound, Fla.

[73] Assignee: Applied Biological Concepts, Los Alamitos, Calif.

[21] Appl. No.: 642,258

[22] Filed: Jan. 16, 1991

[51] Int. Cl.$^5$ .................................................. A61F 2/08
[52] U.S. Cl. ...................................... 128/898; 623/13; 623/20
[58] Field of Search ........................... 128/897–899; 606/86–105; 623/13, 18, 20

[56] References Cited

U.S. PATENT DOCUMENTS

| | | | |
|---|---|---|---|
| 4,585,458 | 4/1986 | Kurland | 128/898 |
| 4,605,414 | 8/1986 | Czajka | 128/898 |
| 4,946,462 | 8/1990 | Watanabe | 128/898 |
| 4,997,434 | 3/1991 | Seedhom et al. | 606/80 |
| 5,139,520 | 8/1992 | Rosenberg | 623/13 |

OTHER PUBLICATIONS

Hewson, *Drill Guides for Improving Accuracy in Anterior Cruciate Ligament Repair and Reconstruction.*, Clin. Orth. Rel. Res. 172:119-124 (Jan.-Feb. 1983).
Lambert, *Vascularized Patellar Tendon Graft with Rigid Internal Fixation for Anterior Cruciate Ligament Insufficiency.* Clin. Orth. Rel. Res. 172:85-89 (Jan.-Feb. 1983).
Rosenberg, *Technique for Endoscopic Method of ACL Reconstruction* (Acuflex Brochure 1989).

Primary Examiner—Kyle L. Howell
Assistant Examiner—J. P. Lacyk
Attorney, Agent, or Firm—Fulwider, Patton, Lee & Utecht

[57] ABSTRACT

A surgical method for arthroscopic repair or replacement of the anterior cruciate ligament is disclosed. A preferred embodiment of the method generally includes forming osseous tunnels in the tibia and femur, opening into the intercondylar region. A patellar tendon graft is harvested from the knee, having bone plugs naturally attached to each end. The graft is secured in the osseous tunnels by an interference fit with a bone screw inserted between the tunnel walls and the bone plugs. Specialized instrumentation for performing the method steps is also disclosed. Such instrumentation includes: a combination drill for cutting an osseous tunnel and harvesting a bone core, an intercondylar guide for locating a pilot hole on the femoral condyle, single-fluted and multi-fluted hand and power reamers for forming an osseous tunnel, and a work station for facilitating preparatory steps performed on graft material.

9 Claims, 9 Drawing Sheets

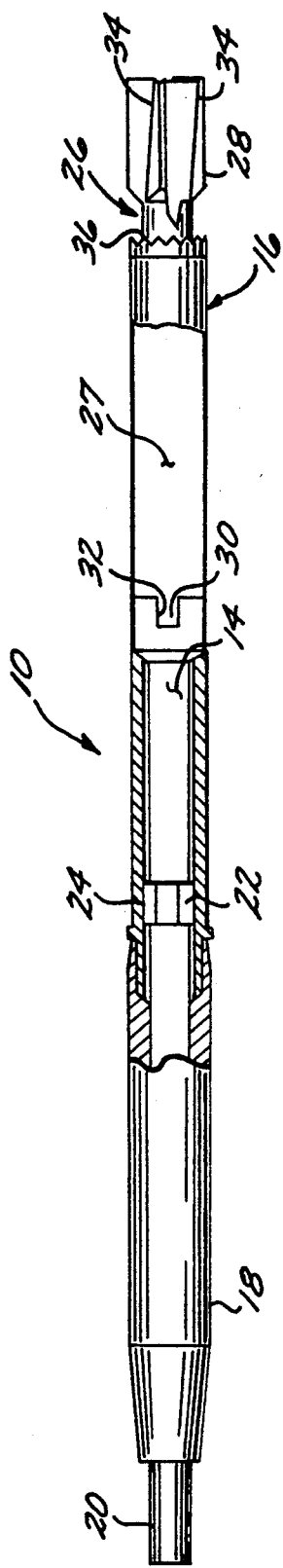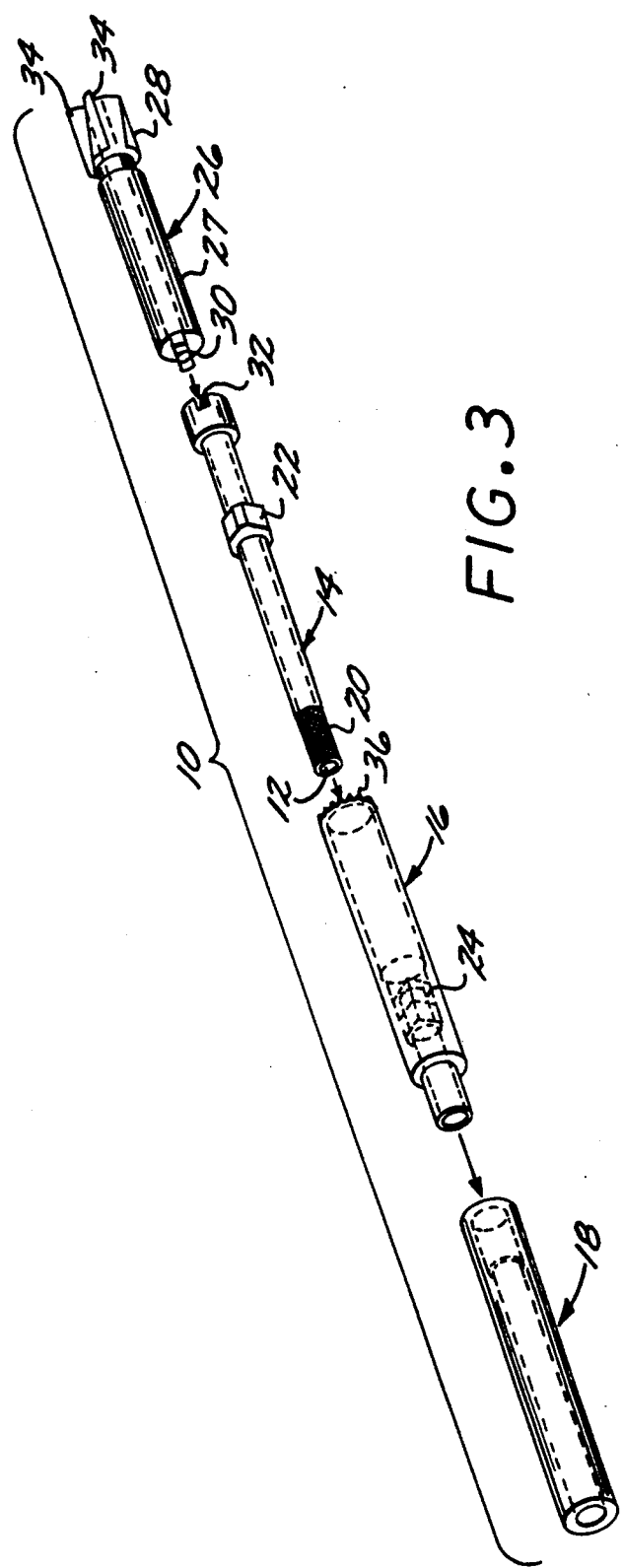

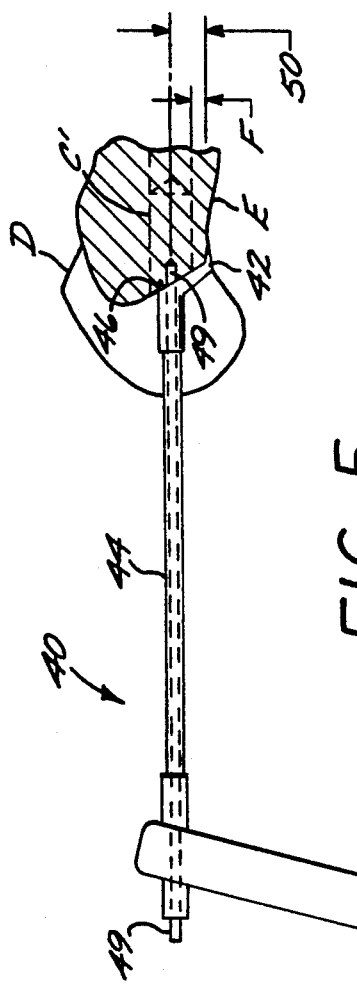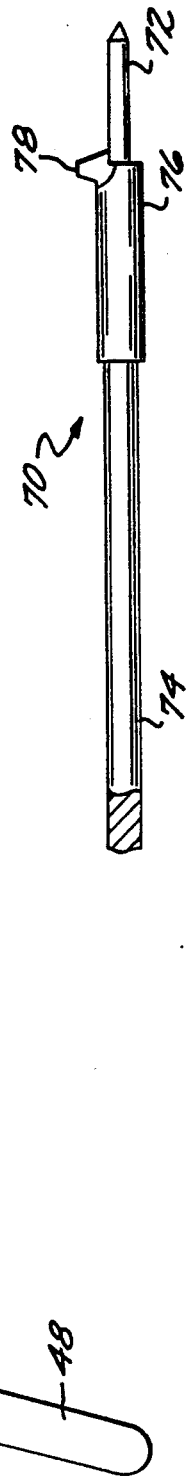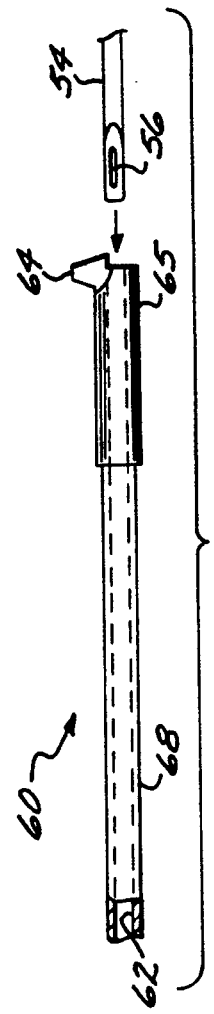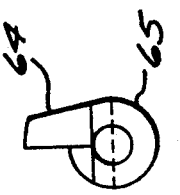

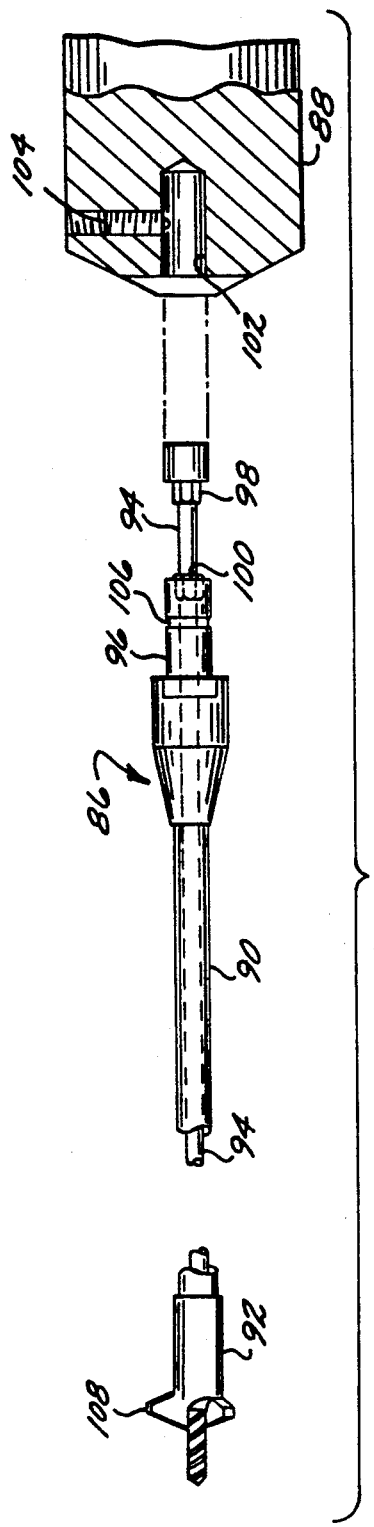
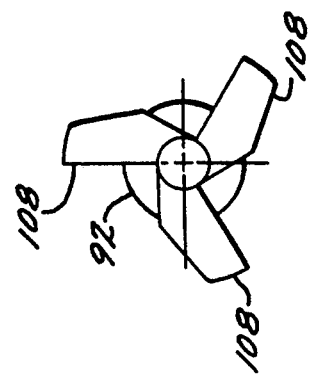
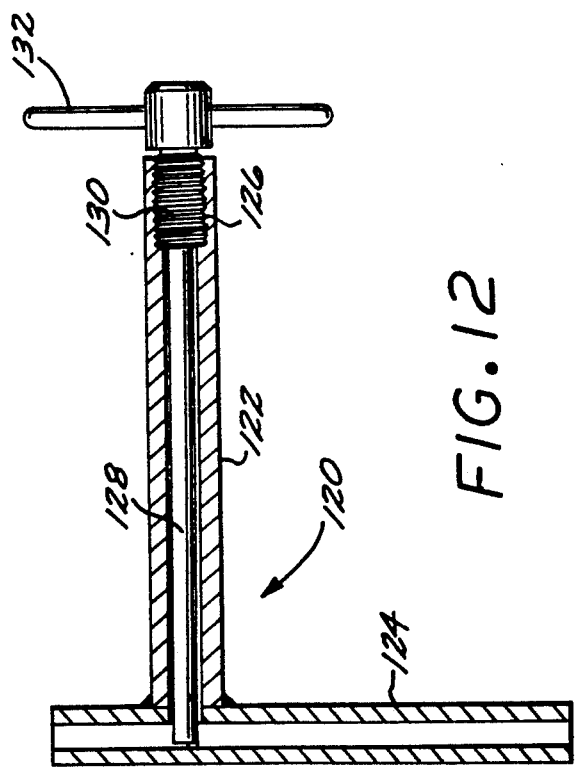
FIG. 10
FIG. 11
FIG. 12

METHOD AND APPARATUS FOR ARTHROSCOPIC KNEE SURGERY

TECHNICAL FIELD OF THE INVENTION

The present invention relates to a method for arthroscopic surgery and apparatus for practicing the method. More particularly, the present invention relates to a surgical procedure for arthroscopic replacement or repair of the anterior cruciate ligament and the instrumentation associated therewith.

BACKGROUND OF THE INVENTION

The basis for deficiencies of the anterior cruciate ligament ("ACL") and various techniques of repair or replacement have been known for many years. See, *The Anterior Cruciate Ligament Deficient Knee*, Clinical Orthopaedics and Related Research, No. 172 (January–February 1983) (J. Feagin, Jr., M. D., Guest Ed.). The great variety of techniques and the non-uniform acceptance of any single technique may have contributed to the lack of specialized instrumentation for performing replacement or repair of the ACL. Instrumentation which has become somewhat specialized in this area is drill guides for locating holes in the tibia and femur. Hewson, *Drill Guides for Improving Accuracy in Anterior Cruciate Ligament Repair and Reconstruction*, Clin. Orth. Rel. Res. 172: 119–124 (January–February 1983) presents a survey of various drill guides. However, none of the drill guides available are without its particular disadvantages.

One technique for the replacement of the ACL, which has gained in popularity in recent years, is the use of a graft taken from the patellar tendon and inserted into tunnels reamed in the femur and tibia. This technique is described in Lambert, *Vascularized Patellar Tendon Graft with Rigid Internal Fixation for Anterior Cruciate Ligament Insufficiency*, Clin. Orth. Rel. Res. 172: 85-89 (January–February 1983). In this the portion of the patellar tendon used is separated from the tibia and patella with a scalpel and osteotome. The osteotome is used to separate the graft with small pieces of bone (to serve as bone plugs) naturally attached at each end of the tendon. One problem associated with this procedure is that the osteotome creates V-shaped defects or recesses where the small bone pieces are removed. The V-shape of the defects can create high stress concentration at those points.

Tunnels or holes are drilled in the tibia and femur, both opening to the intercondylar region. Lambert teaches that the most accurate placement of the holes is achieved by drilling both holes from the outside of the bone towards the inside. Lambert also recommends the use of a Hewson intercondylar drill guide for accurate placement of the holes.

Once the holes have been formed in the tibia and femur, the graft is twisted 180° and pulled through the bone holes by sutures placed through the bone plugs. The twisting of the graft is important to maintain the isometric function of the graft. The ligament graft is secured in place by interference fit of bone screws between the bone hole wall and the bone plug attached to the tendon ends. The procedure as described by Lambert is not arthroscopic.

Rosenberg, *Technique for Endoscopic Method of ACL Reconstruction* (Acufex Brochure 1989), describes a modification of the Lambert technique. The Rosenberg technique is arthroscopic and utilizes a femoral tunnel drilled from below the femur. Rosenberg illustrates the difficulty in locating the center of the femoral tunnel. A method for testing the location to ensure that it will provide proper isometric function of the ligament graft is disclosed, but the location must still be selected without the use of a guide to ensure placement relative to the bone mass in which the tunnel is formed. The location thus depends to a large extent on the skill of the surgeon. While specialized instrumentation is described, it is related only to the method of testing the location for isometric positioning.

Although procedures for repair of the ACL have become relatively common, without special instrumentation, such as guides and reamers, the success of these procedures depends to a greater extent upon the specialized skills of a particular surgeon, more so than if such specialized instrumentation were available. Thus, there has existed a need in the art for a surgical procedure with a range of associated specialized instrumentation to facilitate repair or replacement of the ACL.

SUMMARY OF THE INVENTION

It is therefore an object of the present invention to provide a method, and specialized instrumentation for use with said method, for repair or replacement of the anterior cruciate ligament.

The method according to the present invention generally includes forming osseous tunnels in the tibia and femur opening into intercondylar region. A replacement ligament is inserted through the tibial osseous tunnel and pulled into the femoral osseous tunnel. An end of the replacement ligament is secured in both the tibial and femoral osseous tunnels.

In order to form a tibial osseous tunnel, a guide pin is placed through the tibia to define the center line for the tunnel. The tibial cortical bone center line for the tunnel. The tibial cortical bone surrounding the guide pin is removed and the tunnel is drilled through the cancellous bone. A combination drill for forming the osseous tunnel is part of the present invention. The combination drill includes a reamer connected in line with a core drill. The combination drill is placed over the guide pin to allow the reamer to remove the cortical bone. The combination drill is then temporarily withdrawn from the guide pin and the reamer removed. The combination drill is then replaced over the guide pin to allow the core drill to contact the cancellous bone. Rotation of the core drill cuts the osseous tunnel and simultaneously captures a bone core within the core drill.

Formation of the femoral osseous tunnel begins with locating a pilot hole on the medial face of the lateral femoral condyle. An intercondylar placement guide is provided for this purpose. The placement guide includes a guide tube having a hook shaped means for engaging behind the posterior wall of the femur in the intercondylar region. The engaging means defines a predetermined distance from the posterior wall to the location of the pilot hole. After the pilot hole has been located, it is drilled by inserting a guide drill through the guide tube and into the femur.

Next, a guide hole is drilled in order to guide a femoral reamer for reaming the osseous tunnel. In a preferred embodiment, a power driven femoral reamer has a single cutting flute to facilitate clearing of bone chips and speed the cutting of the device. Alternatively, a hand-operated reamer may be used. The hand-operated reamer includes a distally extending guide drill which cuts the guide hole slightly ahead of the reaming flutes. Use of the hand-operated reamer therefore does not require predrilling of the guide hole.

A patellar tendon-bone graft for replacement of the anterior cruciate ligament may be provided by removing bone plug portions from the tibia and patella with a portion of the patellar tendon naturally attached thereto. A graft harvesting core drill is provided for this purpose. The core drill has a hollow cylindrical body with sharp teeth formed around only a portion of one end of the body. The sharp teeth are placed against the bone in order to cut the bone plug attached to the tendon. The core drill is oscillated in a semi-rotational motion to prevent the sharp teeth from cutting the tendon. The bone plug portion is received in the hollow cylindrical body of the core drill.

Before insertion into the osseous tunnels, the patellar tendon-bone graft is pretensioned and suture receiving holes are drilled in the bone plug portions. A novel work station is provided including apparatus for performing these procedures conveniently attached to a base-plate and thereby secured for easy use and portability. The apparatus include a guide tube and guide tube holder for facilitating sizing and drilling of the holes in the bone plug portion. Also included in the work station are apparatus for splitting a bone core for use as bone graft material and a bone core knock-out block.

BRIEF DESCRIPTION OF THE DRAWING

The features and advantages of the invention will be more readily apparent from the following detailed description of the preferred embodiments, illustrated in the drawing figures, wherein:

FIG. 2 is a partial cross-sectional view of a combination drill according to the present invention;

FIG. 3 is an exploded view of the combination drill of FIG. 2;

FIG. 5 is a side view of the placement guide shown in FIG. 4, illustrating its positioning on the femur;

FIG. 7 is a partial plan view of a femoral reamer according to the present invention;

FIG. 8 is a partial plan view of an alternative embodiment of a femoral reamer according to the present invention;

FIG. 9 is an end view of the femoral reamer shown in FIG. 8;

FIG. 10 is an end view of the femoral reamer shown in FIG. 11;

FIG. 11 is a partial plan view of a hand-operated femoral reamer according to the present invention;

FIG. 12 is a partial cross-sectional view of a drill puller according to the present invention;

FIG. 13A is a plan view of the end of the graft harvesting drill shown in FIG. 13;

FIG. 13B is an end elevation view of the graft harvesting drill shown in FIG. 13;

DETAILED DESCRIPTION OF THE PREFERRED EMBODIMENTS

Figure 6:
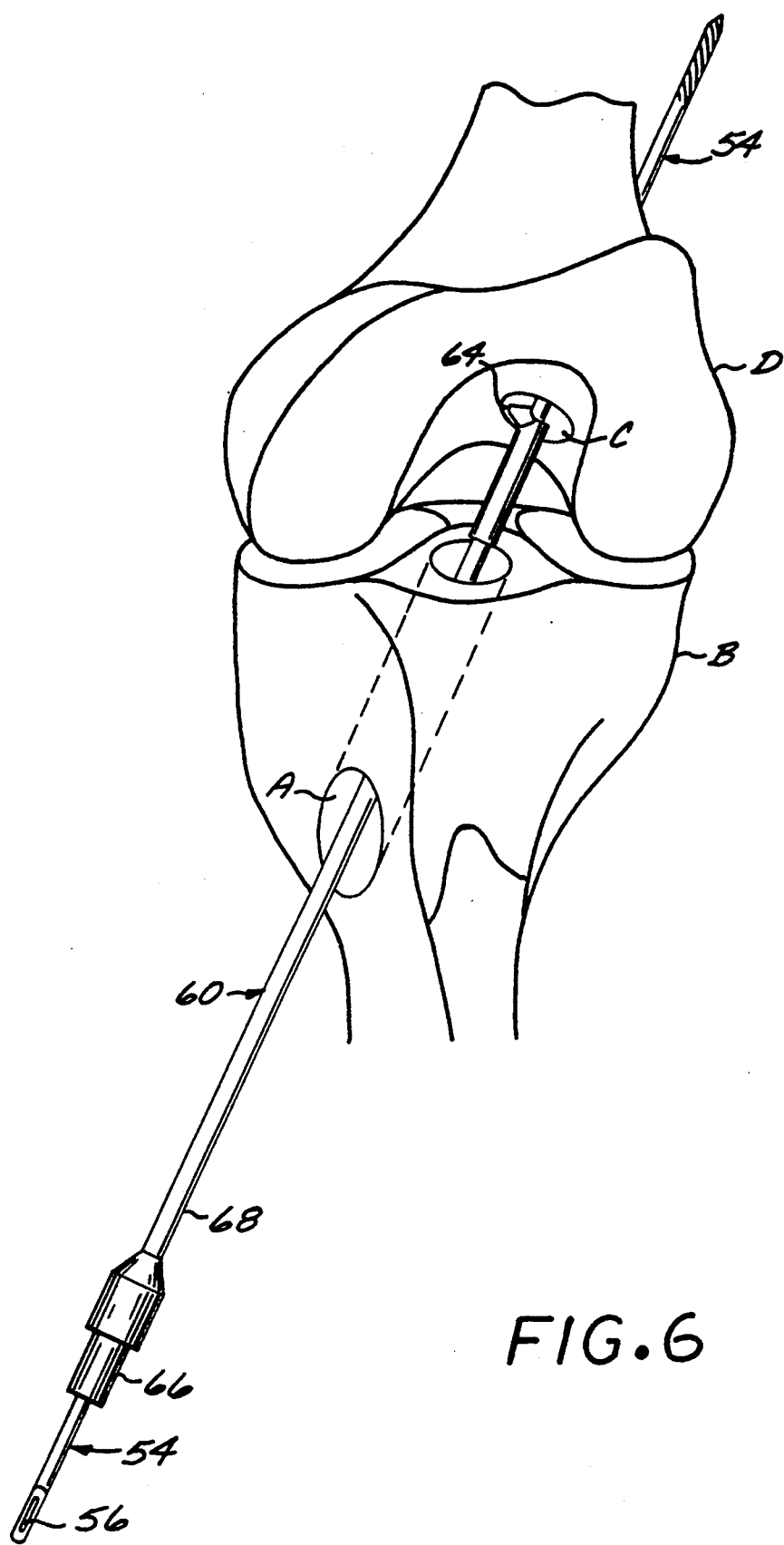
FIG. 6 is a view of a left knee joint, flexed and dissected anteriorly and having tibial and femoral osseous tunnels formed for receiving an ACL graft and also illustrating a femoral reamer and guide drill according to the present invention.

FIG. 6 is initially, briefly referred to in order to introduce the working environment of the present invention. As shown in FIG. 6, replacement of the anterior cruciate ligament ("ACL") requires the formation of osseous tunnel A in tibia B and osseous tunnel C in femur D. A ligament graft (not shown) is then secured between tibia B and femur D by anchoring it in the respective osseous tunnels. A preferred means for anchoring the graft is by interference fit of a bone screw between the osseous tunnel wall and a bone plug attached to the graft end. In this respect, the procedure of the present invention is similar to the Lambert technique described above. The various steps of the procedure, and instrumentation associated with each step, according to the present invention are described in detail below, approximately in the order of performance or use.

A standard tibial drill guide may be used to properly position a guide drill and drill a guide hole for the formation of tibial osseous tunnel A. This is accomplished by standard procedures, understood by those skilled in the art. After the guide drill has been positioned in the tibia, the associated drill guide is removed, with the guide drill left in place. In the prior art, a standard cannulated drill bit would be placed over the guide drill to drill the osseous tunnel. However, as shown in FIG. 1, in the present invention combination drill 10 is placed over guide drill 11 to form tibial osseous tunnel A.

Combination drill 10, shown in detail in FIGS. 2 and 3, is fully cannulated, with cannulation 12 extending throughout its length. Guide drill 11, shown in FIG. 1, is received in cannulation 12. Combination drill 10 includes plunger 14, which extends through core drill 16 and extension sleeve 18. Portion 20 of plunger 14 extends beyond the proximal end of extension sleeve 18 and is received in the chuck of a standard power drill. Plunger 14 has male hex part 22, received in female hex socket 24 in core drill 16, to transmit driving power from plunger 14 to core drill 16. Combination drill 10 also includes reamer 26 at its distal end. Reamer 26 has a cannulated reamer body 27 and fluted head 28. Driving power is transmitted to reamer 26 through key 30, received in slot 32 of plunger 14. Key-slot connection 30, 32 allows reamer 26 and plunger 14 to be removably secured together without relative rotation therebetween.

Figure 1:
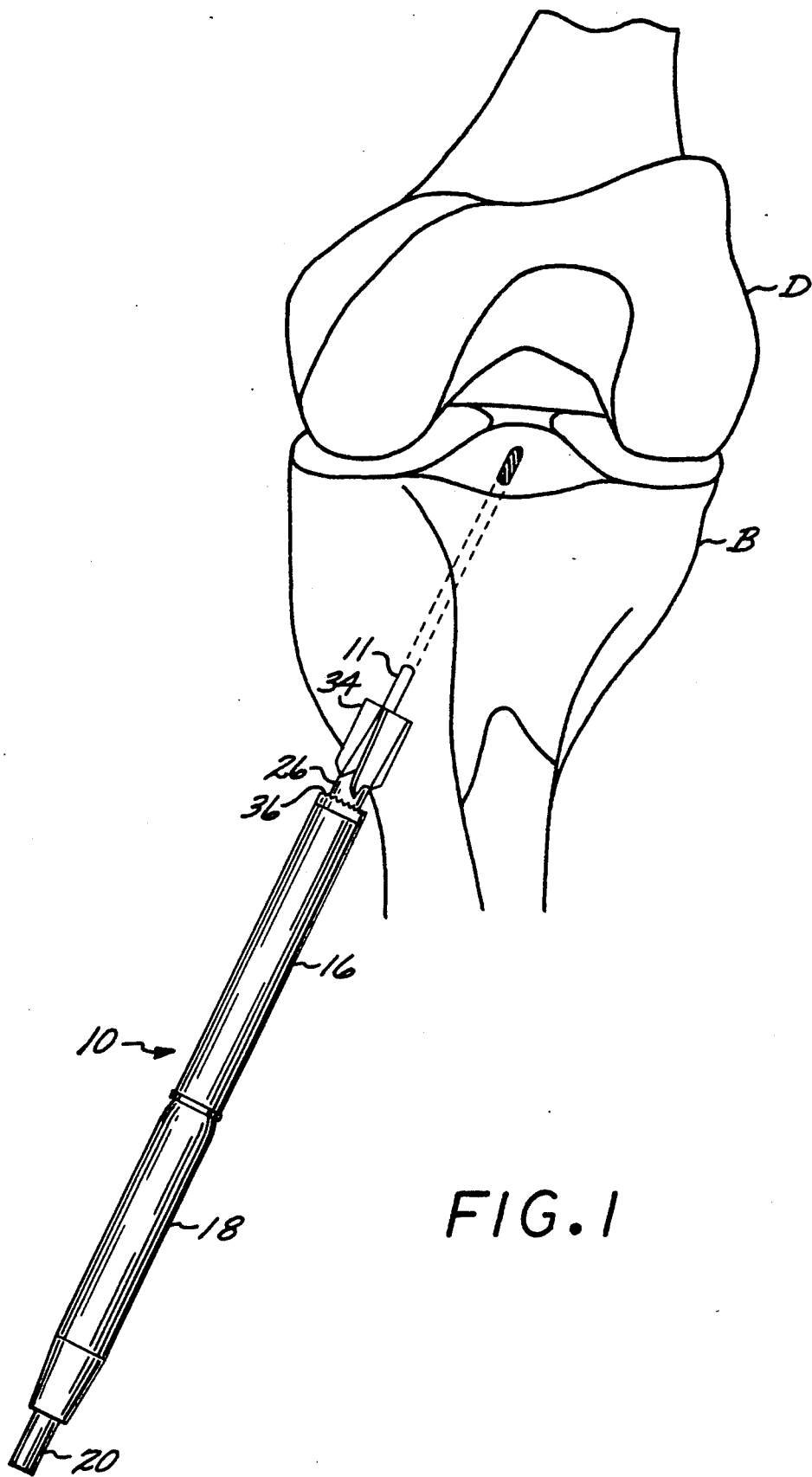
FIG. 1 is a view of a left knee joint, flexed and dissected anteriorly illustrating the positioning of a guide drill and combination drill for forming the tibial osseous tunnel according to the present invention.

In the formation of tibial osseous tunnel A, combination drill 10 is initially utilized with all of the above described components, as shown in FIG. 1. Combination drill 10 is placed over guide drill 11 in the tibia as described. Portion 20 is chucked into a standard power drill (not shown) and rotational power is positively transmitted to reamer 26 through plunger 14 and key slot connection 30, 32. Reamer flutes 34 cut away the cortical bone of tibia B.

Once the cortical bone is removed and the cancellous bone exposed, combination drill 10 is temporarily withdrawn from guide drill 11 and reamer 26 is removed from plunger 14 by disconnecting at key-slot connection 30, 32. Combination drill 10 is then replaced on guide drill 11 with sharpened teeth 36 at the distal end of core drill 16 contacting the cancellous bone of tibia B.

Combination drill 10 is again rotated by the power drill and core drill 16 operates as a hole saw to cut the tibial osseous tunnel A. During the cutting, a unitary bone core (not shown) is received within hollow core drill 16. After the tibial osseous tunnel is complete, the bone core is removed from core drill 16 by removing combination drill 10 from the drill chuck and pushing forward plunger 14 to eject the bone core. The bone core may be saved for use as graft material for repairing bone defects arising from concomitant surgical steps. This use of the bone core is explained in detail below.

Figure 4:
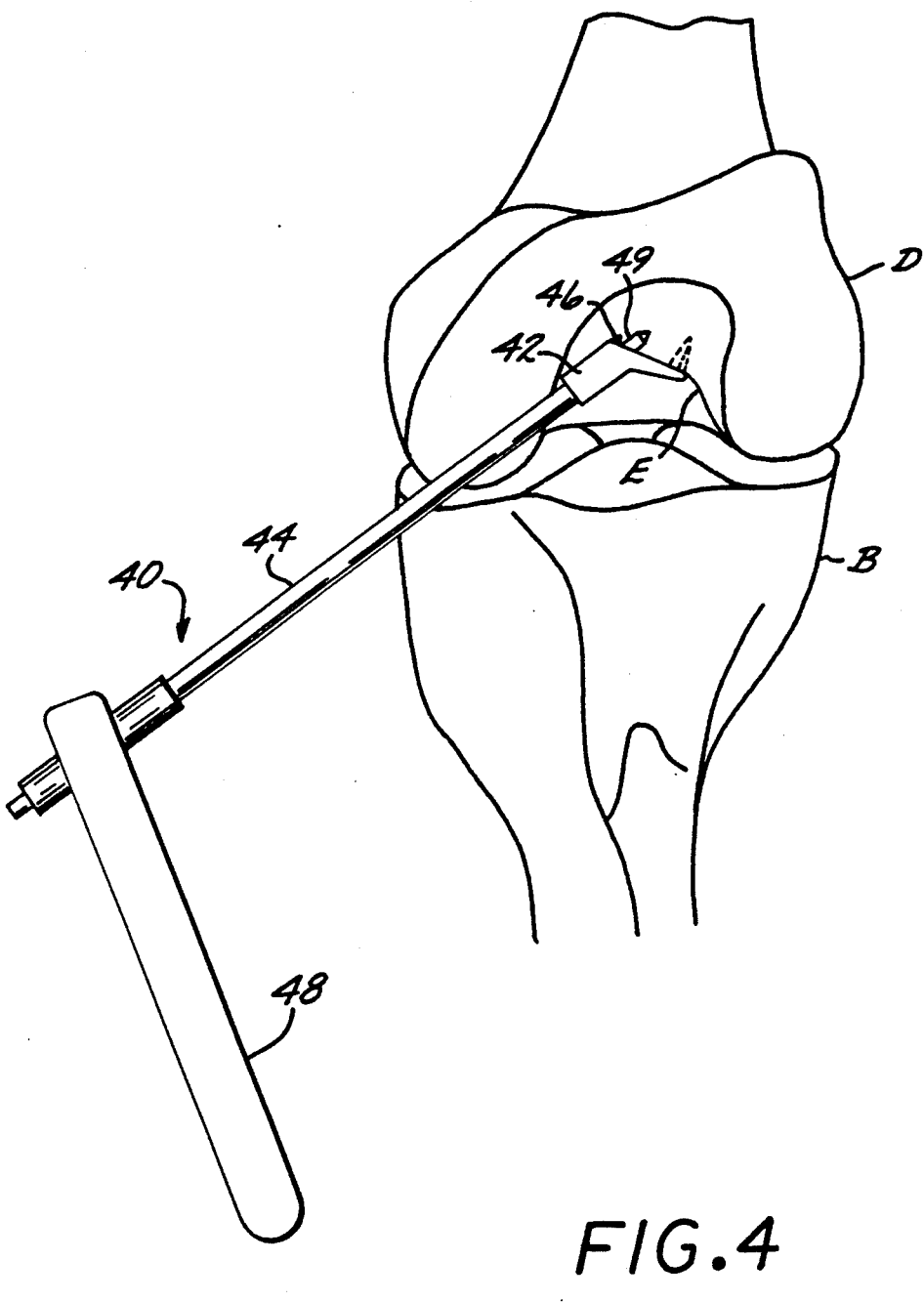
FIG. 4 is a view of the left knee joint, flexed and dissected anteriorly, with an intercondylar placement guide according to the present invention in place on the femur.

After tibial osseous tunnel A is complete, femoral osseous tunnel C is formed. As shown in FIGS. 4 and 5, intercondylar placement guide 40 is used to locate femoral osseous tunnel C with respect to the posterior wall E of femur D in the intercondylar region. The knee is preferably flexed at about 60°, although the exact flexure may vary, depending the size of the knee and particular practice of the surgeon, to beyond 110°. Placement guide 40 helps ensure that the guide hole subsequently drilled enters the cancellous bone and not the medullary canal. Placement guide 40 also helps to guarantee a minimum thickness for the posterior wall of the femoral osseous tunnel. A breakthrough in the posterior wall can make it difficult or impossible to achieve the proper interference fit between the bone screw and bone plug inserted in later steps.

When an ACL is replaced or repaired arthroscopically, it can be difficult for the surgeon to position the femoral osseous tunnel because the location site can not be physically sized or measured to provide specific reference points. Placement guide 40 is placed through a medial port in the knee, generally as shown in FIG. 4. Hook 42, mounted on hollow shaft 44, engages posterior wall E of femur D as shown in FIG. 5. A sharp burr 46 assists in positioning the guide and preventing slippage. Handle 48 facilitates holding the guide.

Once placement guide 40 is in place, guide drill 49, preferably about 2.4 mm in diameter, is inserted through shaft 44 to drill a pilot hole about ¼ inch deep in the intercondylar notch. Again, the knee is preferably flexed at about 60°. The pilot hole marks the center of the osseous tunnel that is to be reamed. It is preferred that the pilot hole be positioned on the medial face of the lateral femoral condyle. Different size intercondylar placement guides are provided by varying the distance between the center of shaft 44 and the inside hook of 42, shown as dimension 50 in FIG. 5. In this manner, the surgeon has the option of selecting the posterior wall thickness F for the osseous tunnel C' to be formed.

Once the pilot hole has been formed with intercondylar placement guide 40, the cortical bone is removed with a known cortical bone reamer by methods understood by persons skilled in the art. The diameter of the cortical bone removed should be the same as the diameter of the femoral osseous tunnel desired.

After the cortical bone has been removed, the surgeon has a number of options in forming femoral osseous tunnel C according the present invention. First, the surgeon must select the approach for reaming the femoral osseous tunnel. Two approaches are possible: a reamer may be inserted through tibial osseous tunnel A, with the knee flexed at about 60° (as shown in FIG. 6), or alternatively, a reamer may be inserted through a medial port in the knee, with the knee flexed at about 90° to allow the reamer to clear the proximal end of the tibia. The latter approach may be required in small knee joints.

Once the approach has been selected, the surgeon must decide whether to use a power or hand reamer. Two alternative embodiments of a power reamer according to the present invention are illustrated in FIGS. 7 and 8. An embodiment of a hand reamer according to the present invention is illustrated FIG. 11. Hand reaming offers technical advantages such as a greater feel for the tunnel as it is reamed, the ability to alter direction of the tunnel and thus greater ease in avoiding the posterior artery. Power reaming has the advantages of speed and minimizing fatigue of the surgeon.

With the power reamer embodiments shown in FIGS. 6, 7 and 8, the surgeon begins by drilling a guide hole using preferably a 2.4 mm guide drill. A preferred guide drill 54, according to the present invention, is shown in FIG. 6. Guide drill 54 has an eye-loop 56 at the trailing end for pulling the ligament graft through tibial osseous tunnel A and into femoral osseous tunnel C. This procedure is described in greater detail below. A standard guide drill may also be used, if desired by the surgeon.

A femoral drill guide (not shown) is used to initially direct guide drill 54. The tubular shaft of a femoral drill guide is inserted into the pilot hole formed in the intercondylar notch. The femoral drill guide is essentially the same as intercondylar placement guide 40, except without hook 42 and burr 46. Guide drill 54 is inserted through the shaft of the drill guide and exits the femur on the lateral posterior side, superior to the condyle, as shown in FIG. 6.

According to the present invention, all drilling and insertion of prosthetic or graft ligaments, is done from below the femoral condyle. Contrary to prior art methods advocating drilling from above the femur, the method of the present invention avoids large lateral incisions necessary to access the posterior lateral side of the femur. Only a small incision is necessary to allow guide drill 54 to be pulled through. The method of the present invention thus also avoids puncturing the posterior capsule.

Referring again to FIGS. 6 and 8, after guide drill 54 has exited the posterior lateral side of the femur, cannulated uni-fluted reamer 60 is placed over the guide drill. The guide drill is received in cannulation 62. Single flute 64 extends radially from reamer body 65 to contact the cancellous bone to be reamed in the formation of femoral osseous tunnel C. Drill connection 66, at the proximal end of shaft 68, is chucked into a standard power drill (not shown). Reamer 60 is then powered through the femur following guide drill 54.

Alternatively, reamer 70, shown in FIG. 7, can be used. With reamer 70, a guide drill such as guide drill 54 is first used to drill a guide hole through the femur in the same manner as explained above. However, after the guide hole is drilled, the guide drill is removed. Reamer 70 has a permanent guide pin 72 and solid shaft 74. Guide pin 72 follows the guide hole and keeps reamer 70 on the correct path. Reamer body 76 and radially extending flute 78 are substantially the same as body 65 and flute 64, except for the absence of a cannulation. Reamer 70 also has a drill connection 66.

The flute configuration of uni-fluted reamers 60 and 70 is illustrated in FIG. 9. The use of a single flute allows the overall mass of the instrument to be significantly reduced, thus facilitating use in the tight-fitting spaces involved in arthroscopic repair of the ACL. The diameter of the femoral osseous tunnel can be varied by changing the length of flute 64 without adding extra mass to the body of the reamer itself. Reamer sizes generally may vary from 5 mm to over 15 mm.

Another advantage of the single flute design is the ability to easily avoid the posterior cruciate ligament ("PCL"). Depending on the size of the knee joint and the particular location of the femoral osseous tunnel, symmetrical prior art reamers or drills used in a similar procedure can interfere with the PCL. Reamers 60 and 70 according to the present invention avoid this problem by allowing the single flute to be rotated away from the PCL as it passes that ligament. Once the flute is safely behind the PCL, the reamer maybe rotated to form the osseous tunnel.

The single flute design of the present invention also provides significant advantages in cutting speed and efficiency. A single flute clears bone chips much faster than multi-flute or standard drill designs known in the art. This allows the osseous tunnel to be drilled much more quickly and reduces chattering of the reamer, which can make the instrument difficult to control.

As discussed above, the surgeon may prefer the use of novel hand-operated reamer 86, shown in FIG. 11. Hand-operated reamer 86 generally comprises removable handle 88, tubular reamer shaft 90 with triple-fluted reamer body 92 and drill coupler 96 attached to reamer shaft 90 opposite reamer body 92. Removable guide drill 94 is slidably received in shaft 90 and has male hex fitting 98 at its proximal end. Hex fitting 98 is received in hex socket 100 at the proximal end of the drill coupler 96. Hex fitting 98 and socket 100 prevent relative rotation between reamer shaft 90 and drill guide 94.

When assembled for use, removable guide drill 94 is inserted into tubular reamer shaft 90 and the proximal end of guide drill 94 is received in socket 102 in handle 88. Handle 88 is provided with spring pin 104, which cooperates with annular detent 106 in drill coupler 96, to secure both guide drill 94 and reamer shaft 90 in handle 88. Placement of reamer shaft 90 into handle 88 forces hex fitting 98 into socket 100 and causes drill 94 to extend about 5 mm distally beyond reamer flutes 108.

To ream the femoral osseous tunnel, the distal tip of guide drill 94 is placed in the pilot hole previously formed in the intercondylar notch. Reamer 86 is rotated by hand and reamer flutes 108 follow guide drill 94 through the cancellous bone.

In a preferred embodiment, hand reamer 86 is provided with a triple-fluted reamer body 92 as shown in FIG. 10. With hand-reaming of femoral osseous tunnel C, three flutes provide greater stability in operation, as opposed to the single flute design preferred for power reaming.

After the osseous tunnels A and C have been reamed, the knee is ready to receive the prosthetic or graft ACL. As explained above, in order to avoid the necessity of a large posterior lateral incision, both osseous tunnels are formed from below. For the same reason, the replacement ligament is also inserted from below. For example, a patellar tendon graft with bone plugs at each end is provided with a suture loop in order to pull it through the osseous tunnel. For this purpose, guide drill 54, shown in FIG. 6 is provided with eye-loop 56 at the trailing end. After the ligament graft is sutured to eye-loop 56, guide drill 54 is pulled out of the femur with eye-loop 56 passing through both osseous tunnels and pulling the ligament graft with it. To assist in pulling guide drill 54 through the femur, drill puller 120, illustrated in FIG. 12, can be employed.

Drill puller 120 comprises two intersecting tubes 122, 124, formed generally in a T-shape. Tube 122 is provided with internal threads 126 at the end opposite the intersection with tube 124. Clamping rod 128 is inserted into tube 122 and provided with threads 130, which mate with internal threads 126. In order to facilitate removal of guide drill 54 from femur D, drill puller 120 is placed over the guide drill by sliding tube 124 onto the guide drill. Handle 132 is rotated to screw clamping rod 128 against guide drill 54 within tube 124. Drill puller 120 is thus temporarily secured to guide drill 54 and provides a simple hand-grip for removal of the guide drill.

Portions of the present invention are directed in particular to the use of a patellar tendon-bone graft as described below. However, a large part of the instrumentation and method described herein is equally useful with other types of prosthetic ligament grafts. Thus, the present invention generally should not be considered as limited only to use with patellar tendon-bone grafts.

Figure 13:
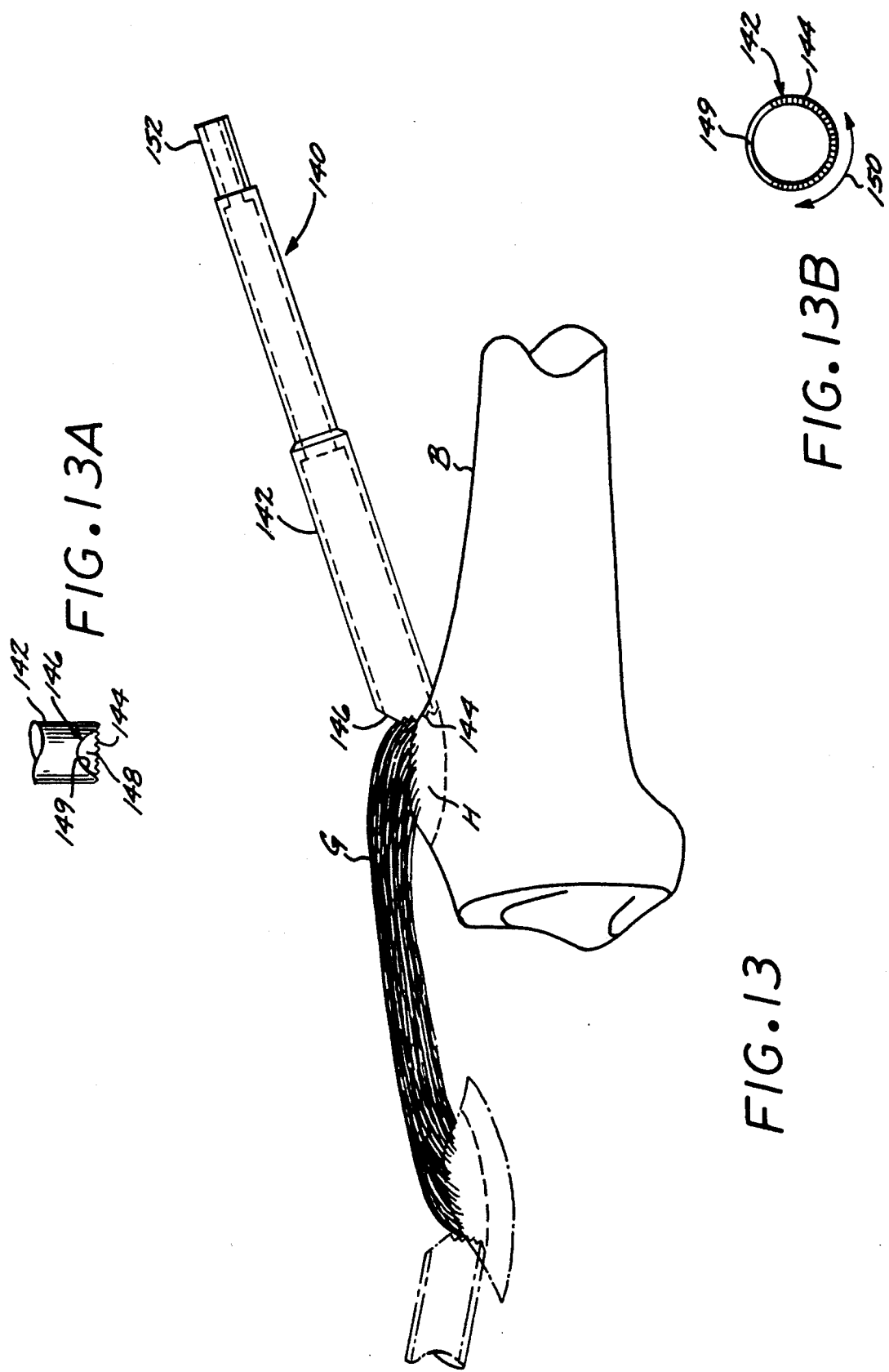
FIG. 13 is a schematic representation of a tibia and patellar tendon, illustrating the features and operation of the graft harvesting drill of the present invention.

FIG. 13 illustrates the procedure and instrumentation for harvesting a patellar tendon-bone graft for ACL replacement according to the present invention. Core drill 140 is shown in place on the tibia B for harvesting the tibial portion of a patellar tendon graft. Also illustrated in phantom lines is the location of drill 140 for harvesting the patellar portion of patellar tendon graft.

Graft harvesting core drill 140 includes a hollow cylindrical body 142 provided with symmetrical sharpened teeth 144 at the end which contacts the bone. Teeth 144 do not extend completely around the circumference at the end of body 142. A portion 146 of the end is chamfered back to provide a notch or recess 148 having rounded edges 149, as shown in FIG. 13A.

Core drill 140 is placed on tibia B in order to harvest a small bone plug H with tendon G naturally attached thereto. The cutting motion of core drill 140 is an oscillating semi-rotational motion as opposed to a full rotational motion. The oscillation of core drill 140 is illustrated by double-headed arrow 150 in FIG. 13B. This back and forth motion is provided by an oscillating power drill into which core drill 140 is chucked at proximal end 152. By oscillating back and forth very rapidly, the core drill achieves the same result as a common rotating drill, but does not risk damage to the tendon. Rounded edges 149 of chamfered portion 146 prevent damage to the ligament graft G as bone plug H is removed.

The patellar tendon is a relatively wide ligament, thus the ligament graft can be removed from the center of the patellar tendon without significantly effecting the function of the patellar tendon, as is known in art. Core drill 140 cuts only the bone and a scalpel is used to separate the tendon portion of the graft from the tendon which is left attached to the tibia and patella. The same procedure is followed to harvest the patellar end of the graft, except that the direction of the drill 140 is reversed.

The diameter of hollow cylindrical body 142 can be varied as desired to allow the bone plug harvested to range in size from smaller than 7 mm to larger than 15 mm in diameter. Whatever size is used, it will be appreciated that the harvesting of the tendon graft in this manner leaves a semi-circular defect in the tibia and the patella. Prior art techniques, using an osteotome, for harvesting the patellar tendon-bone graft leave V-shaped defects which create areas of stress concentration in the tibia or patella. Due to the relative thinness of the patella, stress concentrations can be an especially difficult problem. The semi-circular defects left by the present invention minimize the creation of stress concentrations. Also, the semi-circular defects may be repaired using the bone core resulting from reaming of the tibial osseous tunnel A as discussed above.

If the bone core resulting from the reaming of the tibial osseous tunnel is to be used for repairing defects, a number of preparatory steps must be performed on the bone core. These steps include removing the bone core from core drill 16 and splitting the cylindrical core into semi-cylinders, in order to approximate to outer contour of the bone where the defect is to be repaired.

To prepare to the patellar tendon-bone graft for placement in the osseous tunnels, a number of steps must also first be performed on the graft itself. Small holes must be drilled in the bone plugs of the graft to accept sutures for pulling the graft into place. Also, the graft must be pre-tensioned in order to perform properly after placement.

Figure 14:
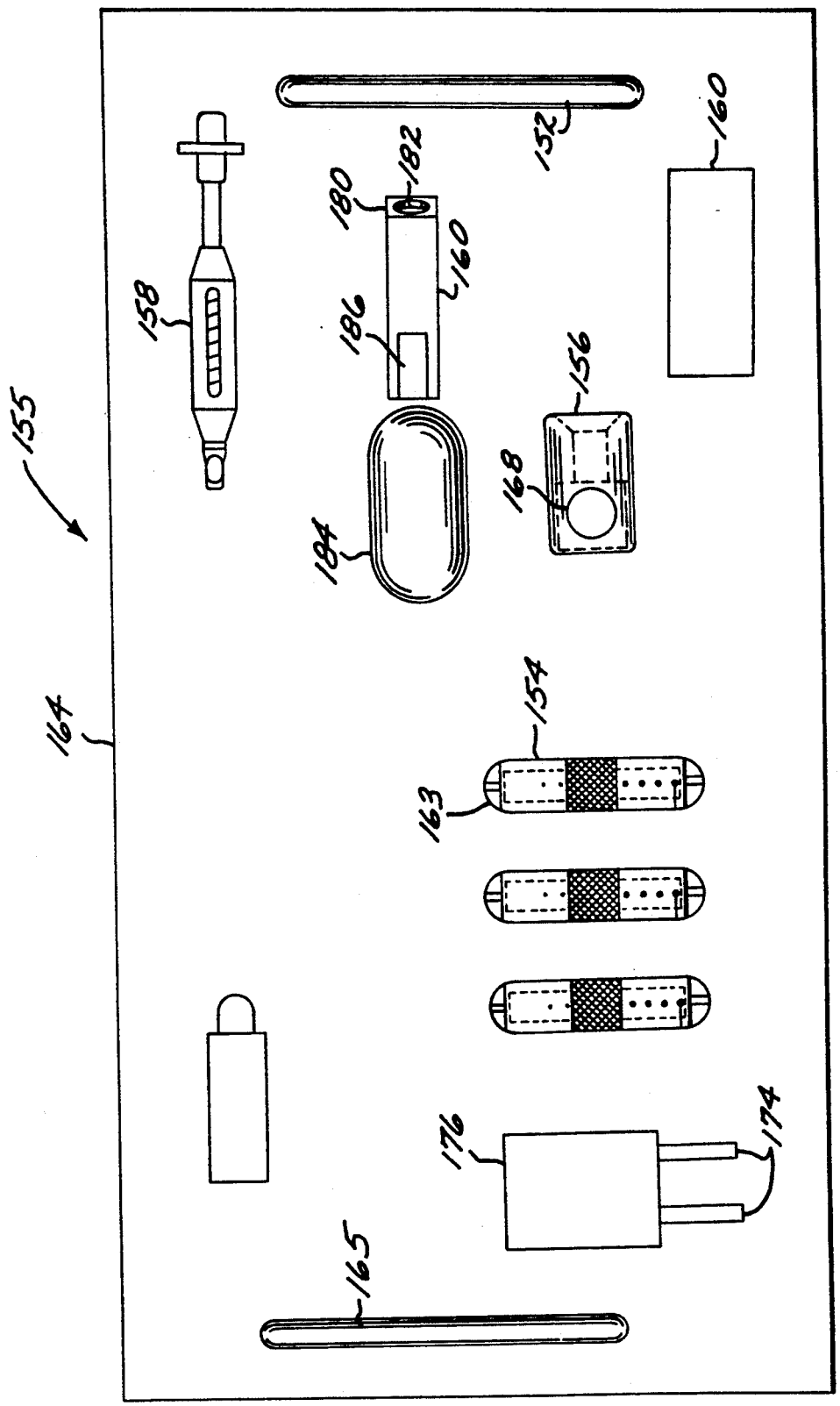
FIG. 14 is a plan view of a portable workstation according the present invention.

In order to facilitate these preparatory steps, the present invention provides a novel work station 155 for simplifying the surgeon's task in each step discussed above. As shown in FIG. 14, work station 155 includes drill guide tubes 154, drill guide tube holder 156, graft tensioner 158, bone core knock-out block 160 and bone core splitter 162. Each of these parts is secured to base plate 164, for the convenience of the surgeon. Base plate 164 preferably may be anodized aluminum. Handles 165 are provided on base plate 164.

Figure 16:
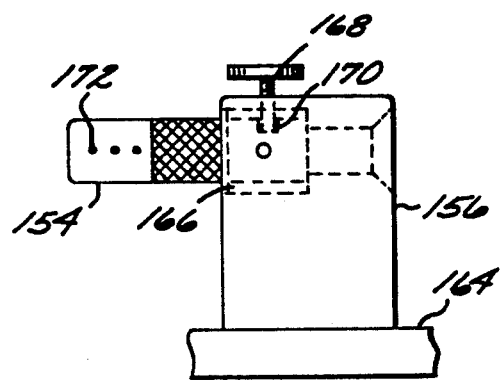
FIG. 16 is a side elevation view of a ligament graft guide tube and tube holder shown in FIG. 14 assembled for use.

One drill guide tube 154 and guide tube holder 156 are shown in detail in FIG. 16. Guide tube holder 156 is secured to plate 164 for stability. Guide tube 154 inserts into bore 166 and is held in place by spring pin 168, cooperating with detent 170. The patellar tendon-bone graft is placed into guide tube 154 with a bone plug adjacent to perpendicular guide holes 172. The surgeon or an assistant may then use hand drills 174, which are snap inserted into block 176 also mounted on plate 164 (FIG. 14), to drill appropriate holes through the bone plug.

A selection of different size guide tubes 154 may be provided to accommodate the different size grafts which may be harvested. The guide tubes are snap fit into recesses 163 in base plate 164 to prevent loss and allow for easy removal.

Graft tensioner 158 may be a standard tensioning device, known to persons skilled in the art.

Figure 17:
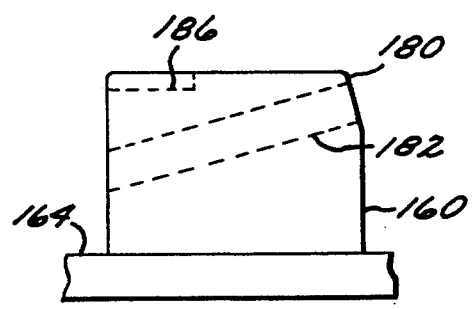
FIG. 17 is a side elevation view of the bone core knock-out block shown in FIG. 14.

Bone core knock-out block 160 is shown in detail in FIG. 17. Block 160 is also securely fastened to plate 164. Block 160 is used for removing the tibial bone core from core drill 16 of combination drill 10 shown in FIGS. 1, 2 and 3. After tibial osseous tunnel A has been drilled, the toothed end of core drill 16 is placed against flat 180 on block 160. Plunger 14 is then used to push the bone core out of core drill 16 into passage 182 in block 160. Passage 182 is inclined at an angle to horizontal to cause the bone core to slide out and fall into depression 184 in plate 164. This design ensures that the bone core does not roll away and thus may be easily handled. A rounded depression 186 may be provided to size the bone core.

Figure 15:
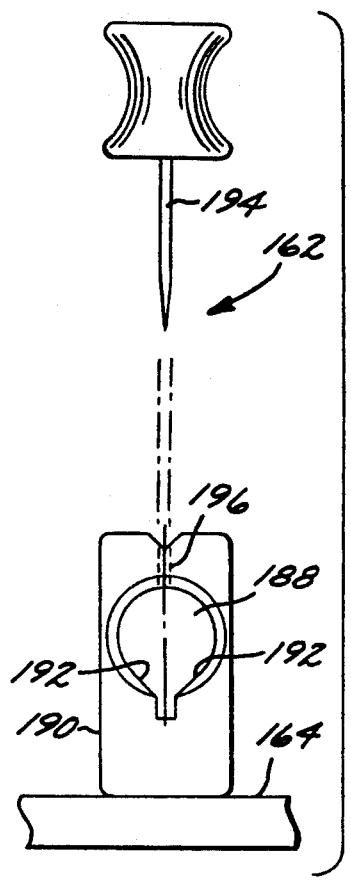
FIG. 15 is an end elevation view of the bone core splitter shown in FIG. 14.

Before the bone core can be used for repairing defects resulting from harvesting the patellar tendon-bone graft, the bone core is split into semi-cylindrical halves with splitter 162 (FIG. 15). The bone core is placed into bore 188 in block 190 of splitter 162. Bore 188 has a flat V-shaped bottom side 192 in order to ensure centering of the bone core. Splitting wedge 194 is then inserted into block 190 through slot 196 to split the bone core. The remaining portion of bone core, left after the core is cut to length, can be used to close the tibial osseous tunnel at the lower end after the ligament graft is in place.

Unless otherwise stated all components of the apparatus according to the present invention are manufactured from medical grade stainless steel, by techniques known to those skilled in the art.

The detailed description of the preferred embodiments contained herein is intended to in no way limit the scope of the invention. As will be apparent to a person of ordinary skill in the art, various modifications and adaptions of the structure above described are possible without departure from the spirit and scope of the invention, the scope of which is defined in the appended claims.

What is claimed is:

1. A method for repair or replacement of an anterior cruciate ligament in a knee of a human subject, comprising the steps of:

forming an osseous tunnel through the tibia;

locating and forming a pilot hole on the medial face of the lateral femoral condyle so as to provide a predetermined posterior wall thickness for an osseous tunnel to be formed extending into the femur centered about said pilot hole;

forming a guide hole through the femur centered about said pilot hole;

forming an osseous tunnel into the femur from the medial face of the lateral femoral condyle centered about said guide hole;

pulling a replacement ligament through the osseous tunnel through the tibia and into the osseous tunnel of the femur via the guide hole; and securing a first end of the replacement ligament in place within the osseous tunnel in the femur and its second end within the osseous tunnel in the tibia.

2. The method of claim 1 wherein a placement guide is used to locate said pilot hole, said placement guide comprising a hollow tube dimensioned to receive a guide drill therethrough and a hook extending from the distal end of said hollow tube, wherein said method further comprises the steps of:

engaging said hook behind the posterior wall of the femur in the intercondylar region; and forming said pilot hole by extending a guide drill through the hollow tube of the placement guide.

3. The method of claim 2 wherein said placement guide further includes a sharp burr extending distally from the distal end of said hollow tube and wherein the method further comprises the steps of engaging the medial face of the lateral femoral condyle with the burr upon engagement of the hook behind the posterior wall of the femur in the intercondylar region in order to prevent slippage of the placement guide once in position.

4. The method of claim 1, further comprising the steps of:
   forming said guide hole through the femur with a guide drill advanced through the osseous tunnel in the tibia, wherein said guide drill has an eyeloop at its proximal end;
   leaving said guide drill in place extending through the femur as the osseous tunnel into the femur is formed thereabout;
   attaching an end of said replacement ligament to said eyeloop; and
   pulling the guide drill out of the femur by its distal end whereby said ligament is pulled through the tibia and into the femur.

5. The method of claim 4, further comprising the steps of:
   placing a single fluted cannulated reamer over the guide drill;
   advancing said reamer through the osseous tunnel in the tibia and to the medial face while positioning the single flute so as to avoid the posterior cruciate ligament; and
   reaming the osseous tunnel into the femur.

6. The method of claim 1, wherein a patellar tendon graft is used as said replacement ligament, further comprising the step of:
   harvesting said patellar tendon by cutting semi cylindrical bone plugs form the patella and tibia under the respective attachment points of the patellar tendon using a core drill oscillating in a semi-rotational motion wherein only about one half of the core drill's leading edge has teeth whereby the tendon is not exposed to the risk of damage and whereby semi cylindrical defects are left in the patella and tibia.

7. The method of claim 6 further comprising the steps of:
   preparing the bone plugs for subsequent introduction, reception and securement within the osseous tunnels in the tibia and femur; and
   maintaining said tendon under tension until such use.

8. The method of claim 6 further comprising the steps of:
   forming said osseous tunnel through the tibia with a core drill capable of capturing a cylindrical bone core formed thereby;
   recovering the captured bone core;
   splitting said bone core longitudinally to provide two semi circular bone core fragments;
   using said semi-circular bone core fragments to repair the semi-cylindrical defects left in the patella and tibia.

9. The method of claim 8 further comprising the steps of:
   cutting a section of cylindrical bone core prior to splitting;
   closing the osseous tunnel through the tibia with said cylindrical bone core section after the tendon end has been secured therein.

* * * * *